(12) United States Patent
Douglas (10) Patent No.: US 9,898,915 B2
(45) Date of Patent: Feb. 20, 2018

(54) TRACKING AND MONITORING APPARATUS AND SYSTEM

(71) Applicant: Raymond Douglas, Newcastle (GB)

(72) Inventor: Raymond Douglas, Newcastle (GB)

(73) Assignee: KINDERGUARD LIMITED, Hollywood (IE)

( * ) Notice: Subject to any disclaimer, the term of this patent is extended or adjusted under 35 U.S.C. 154(b) by 0 days.

(21) Appl. No.: 14/070,784

(22) Filed: Nov. 4, 2013

(65) Prior Publication Data
US 2014/0152435 A1  Jun. 5, 2014

Related U.S. Application Data

(63) Continuation of application No. 10/545,859, filed as application No. PCT/GB2004/000640 on Feb. 17, 2004, now abandoned.

(30) Foreign Application Priority Data

Feb. 17, 2003 (GB) .................................. 0303586.2
Jan. 9, 2004 (GB) .................................. 0400428.9

(51) Int. Cl.
| | | |
|---|---|---|
| *G08B 1/08* | (2006.01) | |
| *G08B 21/18* | (2006.01) | |
| *A61B 5/00* | (2006.01) | |
| *A61B 5/0205* | (2006.01) | |
| *A61B 5/08* | (2006.01) | |
| *G01S 5/00* | (2006.01) | |
| *G08B 21/02* | (2006.01) | |

(52) U.S. Cl.
CPC ............ *G08B 21/18* (2013.01); *A61B 5/0006* (2013.01); *A61B 5/02055* (2013.01); *A61B 5/0816* (2013.01); *G01S 5/00* (2013.01); *G08B 21/0211* (2013.01); *G08B 21/0261* (2013.01); *G08B 21/0269* (2013.01)

(58) Field of Classification Search
CPC ..... G06F 17/327; A61B 5/721; A61B 5/0205; A61B 5/08; A61B 5/021; A61B 5/024; A61B 5/681; H64L 63/0861; G07C 9/00087
USPC ..... 340/537.1, 539.1–539.19, 5.8, 5.52, 438, 340/57.1, 5.82; 600/300, 301; 128/903–905, 920
See application file for complete search history.

(56) References Cited

U.S. PATENT DOCUMENTS

| | | | | |
|---|---|---|---|---|
| 5,652,570 | A * | 7/1997 | Lepkofker | ............ A61B 5/1112 340/407.1 |
| 5,724,025 | A * | 3/1998 | Tavori | .................. A61B 5/0002 340/573.1 |
| 5,825,283 | A * | 10/1998 | Camhi | .................. B60R 25/102 340/438 |
| 6,028,514 | A * | 2/2000 | Lemelson et al. | ........ 340/539.13 |
| 6,034,622 | A * | 3/2000 | Levine | ................. A61B 5/0031 340/3.7 |

(Continued)

*Primary Examiner* — Hoi Lau
(74) *Attorney, Agent, or Firm* — Preston Smirman; Smirman IP Law, PLLC (57) ABSTRACT

A programmable mobile unit for a portable host, such as a person, comprising a microcontroller in communication with each of a detachable freespace communication module for communication with a control center, a GPS unit for communication with at least a GPS satellite system and a biometric sensor for monitoring and identifying the host.

28 Claims, 3 Drawing Sheets

(56) References Cited

U.S. PATENT DOCUMENTS

| | | | | |
|---|---|---|---|---|
| 6,072,396 A * | 6/2000 | Gaukel | B60R 25/1004 | |
| | | | 340/5.5 | |
| 6,134,340 A * | 10/2000 | Hsu | G06K 9/6203 | |
| | | | 382/124 | |
| 6,198,394 B1 * | 3/2001 | Jacobsen | A61B 5/1112 | |
| | | | 340/10.1 | |
| 6,218,945 B1 * | 4/2001 | Taylor, Jr. | A61B 5/0002 | |
| | | | 340/539.1 | |
| 6,426,719 B1 * | 7/2002 | Nagareda | G01C 21/20 | |
| | | | 340/573.1 | |
| 6,512,456 B1 * | 1/2003 | Taylor, Jr. | A61B 5/1112 | |
| | | | 340/539.1 | |
| 6,540,674 B2 * | 4/2003 | Zadrozny et al. | 600/300 | |
| 6,569,094 B2 * | 5/2003 | Suzuki et al. | 600/300 | |
| 6,579,231 B1 * | 6/2003 | Phipps | A61B 5/0002 | |
| | | | 128/903 | |
| 6,747,561 B1 * | 6/2004 | Reeves | G06F 1/1626 | |
| | | | 340/573.1 | |
| 6,762,684 B1 * | 7/2004 | Camhi | G08B 21/0211 | |
| | | | 340/573.1 | |
| 6,847,892 B2 * | 1/2005 | Zhou | G01S 5/0027 | |
| | | | 340/426.1 | |
| 6,893,396 B2 * | 5/2005 | Schulze et al. | 600/300 | |
| 7,124,300 B1 * | 10/2006 | Lemke | G06F 21/32 | |
| | | | 340/5.53 | |
| 8,475,367 B1 * | 7/2013 | Yuen | G06F 19/3418 | |
| | | | 128/920 | |
| 2002/0053857 A1 * | 5/2002 | Scott | G06K 9/0002 | |
| | | | 310/314 | |
| 2002/0145559 A1 * | 10/2002 | Sullivan | G07C 1/10 | |
| | | | 342/357.74 | |
| 2003/0135097 A1 * | 7/2003 | Wiederhold | A61B 5/02055 | |
| | | | 600/301 | |
| 2003/0173408 A1 * | 9/2003 | Mosher, Jr. | A61B 5/117 | |
| | | | 235/492 | |
| 2003/0174049 A1 * | 9/2003 | Beigel | G06K 19/0716 | |
| | | | 340/10.42 | |
| 2004/0100376 A1 * | 5/2004 | Lye | A61B 5/411 | |
| | | | 340/539.12 | |
| 2005/0203349 A1 * | 9/2005 | Nanikashvili | 600/300 | |
| 2009/0058635 A1 * | 3/2009 | LaLonde | A61N 1/37282 | |
| | | | 340/539.11 | |
| 2014/0089673 A1 * | 3/2014 | Luna | H04L 63/0861 | |
| | | | 713/186 | |

* cited by examiner

TRACKING AND MONITORING APPARATUS AND SYSTEM

CROSS-REFERENCE TO RELATED APPLICATION

The instant application is a Continuation of U.S. patent application Ser. No. 10/545,859 filed Aug. 17, 2005, pending, a national phase of PCT International Application No. PCT/GB2004/000640, filed on Feb. 17, 2004, and claims priority to GB Patent Application Serial No. 0303586.2, filed on Feb. 17, 2003 and GB Patent Application Serial No. 0400428.9, filed on Jan. 9, 2004, the entire specifications of all of which are expressly incorporated herein by reference.

The present invention relates to a tracking and monitoring apparatus and system and in particular to an apparatus and system for tracking and monitoring people who operate in a plurality of different environments.

The price of GPS units has dropped dramatically over the last number of years to such an extent that modern automobiles and watercraft have GPS units installed to assist the operator with navigation. Due to the increase in reported cases of child abduction in recent years as a result of the globalisation of large media companies in addition to the increase in popularity of so-called dangerous sports, such as mountain-climbing or off-piste skiing, which generally require remote locations, it has also become desirable to provide people with GPS tracking units. These units are particularly useful if the person wearing the unit is in distress and is able to generate a distress signal by activating an alarm on the unit.

The distress signal can be transmitted from the unit and a search and rescue team are able to accurately identify the whereabouts of the person in distress before attempting a rescue.

One disadvantage associated with tracking devices of the prior art is that they are dependent upon the host to transmit distress signals. The GPS tracking units of the prior art are passive devices which interact with satellites only. In addition to this, there is a significant risk that if the tracking unit falls off a host and generates a distress signal as it hits the ground or is later interfered with by someone else or a wild animal, for example, the distress signal does not provide an accurate indication of the current location of the host but instead gives the location of the unit itself.

It is an object of the present invention to obviate or mitigate the problems of prior art tracking units outlined above.

Accordingly, the present invention provides a programmable mobile unit for a portable host, such as a person, comprising a microcontroller in communication with each of a detachable free space communication module for communication with a control centre, a GPS unit for communication with at least a GPS satellite system, and a biometric sensor for monitoring and identifying the host.

Preferably, a set of communication modules are provided for use with the mobile unit and each module is configured to interface with different wireless protocols.

Ideally, the protocols include GPS, GSM, GPRS, Mode, 3G-UMTS and IEEE 802.11 WLAN. Advantageously, this allows various different types of mobile unit to be deployed in different situations such as enclosed theme parks, chemical plants or outdoor pursuits.

Preferably, the microcontroller has a control program stored thereon for receiving information from the GPS unit and the biometric sensor and storing the information in a local memory.

Ideally, the microcontroller has a database of acceptable behaviour parameters for the host stored in the memory of the unit. This database defines the boundaries of acceptable behaviour for the host including acceptable geographical locations for the host in addition to acceptable biological values such as body temperature and/or heart rate and/or bioelectrical impedance at any given point in time.

Preferably, the microcontroller has a control program stored thereon for comparing information received from the GPS unit and the biometric sensor against the behaviour parameters database stored in on-board memory for a given host at any given time. Ideally, the microcontroller is pre-programmed to periodically monitor and download up-to-date information from the GPS unit and the biometric sensor.

Preferably, the control program loaded in the memory of the microcontroller runs the information received from the GPS unit and the biometric sensor against the behaviour parameters database every time new location and biometric information is captured and downloaded from both the biometric sensor and the GPS unit.

Ideally, exception values falling outside allowable tolerances defined in the database are detected by an interpretation program also stored in the memory of the microcontroller.

Preferably, the interpretation program has means for prioritising these exception values and has means for selecting values which indicates that the host is encountering significant difficulties.

Ideally, the microcontroller transmits these selected values via the communications module to a control centre.

Alternatively, the microcontroller transmits these selected values via the GPS unit.

Ideally, the behaviour parameters database is remotely programmable to take new activities and routines of the host into account.

Preferably, the biometric sensor comprises a power source and a plurality of body contacting elements.

Ideally, the body contacting elements provide information indicative of activity of the host such as, body temperature, heart rate and respiration.

Preferably, the biometric sensor and the microcontroller communicate using bluetooth technology.

Ideally, the biometric sensor and microcontroller are configured to uniquely identify the host from biological data specific to the host during a learning phase when the sensor is first placed on the host and the unit is initially powered up.

Preferably, this unique identification is a biometric signature for the host and is used to benchmark subsequent data feeds from the biometric sensor.

Ideally, the biometric sensor is provided by a flexible multi-sensor patch which monitors ECG, temperature and respiration rate continuously. The sensor-based patch is disposable, low cost and user friendly, similar to current disposable ECG electrodes. The sensor patch is small and low profile, capable of being worn in a completely non-invasive manner.

Preferably, the device integrates patented screen printable ECG electrode technology with new micro-thermistors and piezo-electric based respiration sensors.

The patch is easily applied and remotely monitorable utilising freespace based communications such as Bluetooth. It is capable of connectivity with the microcontroller either directly via a serial interface as part of an integrated solution, or using Bluetooth as part of an optional upgrade solution.

Preferably, the biometric sensor is provided with flexible circuitry to allow the sensor to adapt to the shape of the host's body.

In another embodiment of biometric sensor, the microcontroller has means for generating and transmitting signals into the body of the host and means for receiving and analysing the signals from the host's body via the biometric sensor, the signals being attenuated by bioelectrical impedance of the host's body whereby in use the analysis of the attenuated signals by the controller provides a bioelectrical impedance signature capable of uniquely identifying the host.

Bioelectrical impedance is measurable with simple technical instruments which facilitates the ability to miniaturise the biometric sensing technology to a degree suitable for implementation.

Ideally, the biometric sensor comprises two or more electrodes disposed on the host's skin. Preferably, the means for generating and analysing signals comprises a software control module stored on the memory of the microcontroller, being executable on the processor.

Live biometric data describes information obtained from the person the sensor is currently mounted on as opposed to information from the person whose biometric data was originally recorded during a learning phase when the mobile unit is first put on.

Preferably, a host's bioelectrical impedance signature is stored on the memory of the mobile unit, this signature being recorded during initial enrolment and primary data calibration in a secure environment or during the learning phase as for the other biometric signatures.

Ideally, the software control module is capable of comparing the live bioelectrical impedance signature recorded with the bioelectrical impedance signature recorded during enrolment or learning phase.

Ideally, the software control module has error identifying means comprising robustly designed algorithms taking into account skin resistivity, sweat, geographical regionality, weight, age, gender, current, voltage measurement and frequency range.

Preferably, the biometric sensor has circuitry capable of generating a range of analogue signals of varying currents and frequency.

Essentially, the currents are of a magnitude to ensure safe passage through a hosts body. Ideally, the currents are in the range of 100 µA to 900 µA.

Preferably, the frequency of the signals is in the range of 1 to 1350 KHZ.

Ideally, the software control module has means for identifying bioelectrical impedance characteristics representative of fat mass, body cell mass, extracellular water and skeletal mass.

Preferably, the software control module is capable of generating, transmitting, receiving and analysing signals in a time interval in the range of a few seconds to provide a host identified or host not identified output.

Ideally, the time interval is approximately one second.

Ideally, the biometric sensor circuitry has means for reading attenuated signals from one or more electrodes.

Preferably, the sensor circuitry has means for filtering the signal, converting the analogue signal to a digital signal and passing the signal to the processor for analysis.

Preferably, the algorithms have means of generating a unique bioelectrical impedance signature for a specific host from a full set of data including skin resistivity, sweat, geographical regionality, weight, age, gender, current, voltage measurement and frequency range. The algorithms may combine the impedance with other biometric data as may be required.

Ideally, the algorithms are capable of reducing the time required to identify a live host by utilising a subset of data selected from any combination of the above variables.

The present invention also provides a method of uniquely identifying a host comprising the steps of a controller generating and transmitting signals into the body of a host, the controller receiving signals from the host's body after they have been attenuated by the bioelectrical impedance of the host's body, the controller analysing the attenuated signals to produce a bioelectrical impedance signature capable of uniquely identifying the host.

Ideally, the method also comprises the step of the controller comparing a bioelectrical impedance signature of a host recorded during secure enrolment or the learning phase with a live bioelectrical impedance signature recorded from the current host's body for identification purposes.

Preferably, the method comprises generating and transmitting an electrical current over a range of frequencies into the host's body via at least one electrode and receiving the attenuated signal via the or each electrode, the sensor circuitry reading the resulting voltage drop for each frequency of the signal, filtering the attenuated signal, converting the signal from analogue to digital and passing the digital signal to the processor.

Preferably, the host wears the programmable mobile unit as jewellery or clothing with the electronic components incorporated therein. This type of equipment is commonly referred to as smart clothing.

Preferably, the mobile unit includes a Wide Area Augmentation System (WAAS). WAAS is a twelve channel receiver for improving the accuracy and integrity of GPS signals. Ideally, the mobile unit has means for shielding itself from electromagnetic interference and other environmental signal interference sources.

Ideally, the mobile unit supports an Application Programmers Interface (API) scripting language and graphical user interface (GUI). Advantageously, these features allow the definition of the acceptable behaviour rules regarding geographical location of the host relative to time and the upper and lower tolerances of the biometric data.

The present invention also provides a system for monitoring and tracking a host, such as a person, comprising a control centre in freespace communication with a mobile unit and a GPS satellite system, the mobile unit comprising a microcontroller in communication with each of a detachable freespace communication module for communication with the control centre, a GPS unit for communication with at least a GPS satellite system, and a biometric sensor for monitoring and identifying the host.

Preferably, the control centre of the system and interested third parties are in communication via fixed/freespace communication protocols.

Ideally, the protocols include GPS, IBEE 802.11, GSM, iMode, ISDN, Internet, PSTN and Bluetooth.

Ideally, the mobile unit communicates with the control centre using freespace communication protocols.

Preferably, the protocols include GPS, IBEE 802.11, GSM, iMode and Bluetooth.

Ideally, an earth transceiver station is provided for communicating signals between the satellite system and the control centre.

Preferably, the acceptable behaviour database is also stored at the control centre for further analysis of exception values reported from the mobile unit.

Ideally, the system includes a web-based interface to a database driven secure environment for dynamic creation and modification of the acceptable behaviour database stored in the control centre and the mobile unit.

Preferably, the control centre includes means for alerting custodians and interested third parties of exception values via chosen fixed/freespace communication protocols.

Ideally, the behaviour rules are defined in software agents via a web-based GUI and downloaded to the mobile unit.

Preferably, the system has means for identifying that the mobile unit is no longer functioning or the mobile unit has lost contact with the host. Separation is recognised as the biometric sensor takes readings every 30 seconds and if no biosignals are received for an extended period of time then either the biosensor is no longer attached to the host or there is a malfunction with the mobile unit's communication system.

The present invention also provides a second programmable mobile unit for tracking and monitoring a portable host comprising a microcontroller, a database stored in a memory of the microcontroller containing acceptable behaviour data for the host, a GPS location unit in communication with the microcontroller, a control program loaded in the memory of the microcontroller for detecting when signals from the GPS unit contain exception values which fall outside the parameters defined in the acceptable behaviour database.

Preferably, the database contains acceptable geographical location data and acceptable biological data as a function of time for a specific host.

Ideally, the second mobile unit also has a biometric sensor in communication with the microcontroller.

Preferably, the control program detects when signals from the biometric sensor contain exception values which fall outside the acceptable biological parameters defined in the acceptable behaviour database.

Ideally, the second programmable mobile unit is suitable for use with the system described above.

Preferably, both mobile units have means for supporting European Geostationery Navigation Overlay Service (EGNOS).

The present invention further provides a control program for controlling the operation of the monitoring and tracking system having means for generating and transmitting signals, interrogation means for receiving signals from a plurality of input means, interpretation means for analysing signals received from the interrogation means and alarm generating means operable in response to identification of exception values by the interpretation means.

Ideally, the signals received from input means include OPS input data and biometric input data.

Preferably, the interpretation means comprises a database of acceptable biological and geographical data for a host as a function of time and a set of encoded instructions for processing information captured from the GPS input data and biometric input data against the database to check for biological and geographical exception values falling outside acceptable tolerances defined by the database.

Ideally, the means for generating, transmitting and receiving signals includes encoded instructions for controlling the GPS transceiver and the communications module via a microprocessor.

Preferably, the set of encoded instructions of the interpretation means are terminate and stay resident software agents communicable between the mobile unit and the control centre.

The invention will now be described with reference to the accompanying drawings, which show by way of example only one embodiment of a programmable mobile unit and one embodiment of a system for monitoring and tracking a host wearing the mobile unit. In the drawings.

Figure 1:
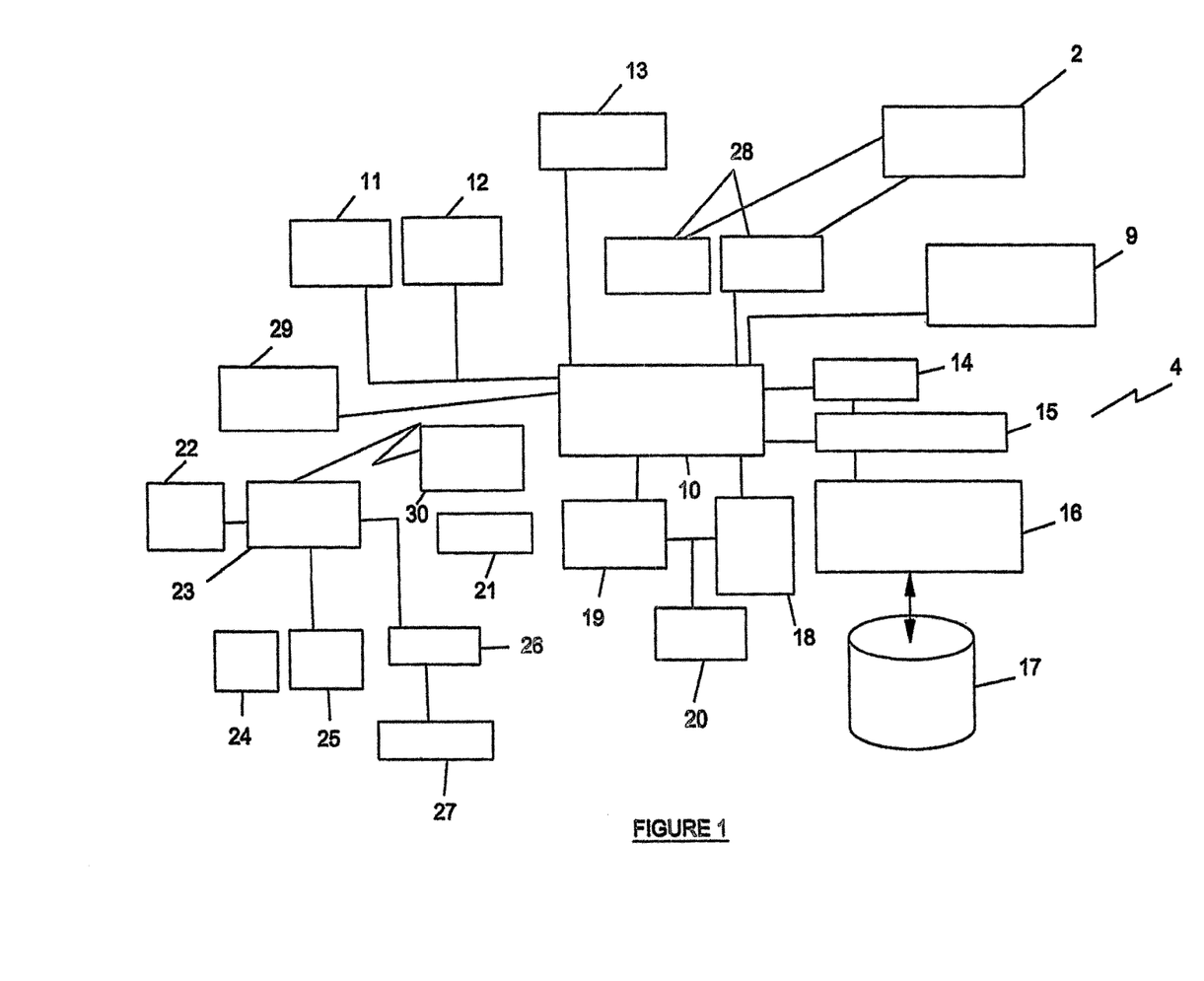
FIG. 1 is a schematic drawing of the architecture of a programmable mobile unit.

Referring to the drawings and initially to FIG. 1 there is shown a programmable mobile unit indicated generally by the reference numeral 4. The unit 4 has a central microprocessor 10 (ARM) processing signals received by the unit 4. The processor 10 has a clock 21 and a power source 19 which also provides power for the GPS transmitter/receiver pair 28. The level of the power source 19 is constantly monitored by a power level sensor 18. A solar cell 20 is connected to the power source 19 providing an effective back-up storage supply in the event that the power source 19, such as a battery, runs flat. The processor 10 is able to sense the power level of the power source 19 and initiate a reduced power mode when appropriate.

A local memory 14 is provided for storing data obtained from a biometric sensor 23 and information received from the GPS receiver 28. The biometric sensor 23 has a power source 22 and includes a number of detectors 24, 25, 26 and 27 for receiving various information representing physical attributes of the hosts body such as skin type 24, body temperature 25, ECG 26 and respiration 27.

A logic and control unit 15 is in communication with the local memory 14 and the processor 10 and the logic and control unit 15 is also in communication with software 16 (terminate and stay resident agents TSR's). A database 17 is also stored in the memory 14 of the unit 4 containing a predetermined set of acceptable behaviour parameters which are used to benchmark the dynamic information received from the biometric sensor 23 and the GPS receiver 28.

Microprocessor 10 is also in communication with and controls the operation of a communications module 9 and a GPS transmitter/receiver pair 28. A manually actuatable alarm 12 is located on the unit 4 allowing a host to transmit a distress signal via either the GPS transmitter 28 or the communication module 9. If the alarm 12 is activated by accident or the event causing the distress has passed, the host can de-activate the alarm by pressing the alarm disarm button 11. The mobile unit 4 also includes a radio frequency pulse generator 13 connected to the processor 10. This generator 13 facilitates close quarter detection.

In use, prior to normal operation of the mobile unit 4 the biometric sensor 23 is calibrated against the physical attributes of the specific host. At initiation, the biometric sensor 23 detects a number of key parameters including skin type 24, ECG 26, body temperature 25 and body respiration 27. After an initial learning period the biometric sensor 23 enters normal operation mode. During the learning period, the biometric sensor 23 issues signals to the processor 10 of the mobile unit 4 using bluetooth technology. Within processor 10 there is logic and control to process the biometric data during these 30-60 seconds of the learning period. After this period has elapsed, the processor 10 creates a packet data unit (PDU) and transmits the combined biometric signals as a biometric signature 29 of the host to a control centre (see FIG. 2). Thereafter, the biometric signature 29 is used to monitor subsequent data feeds from the host and identifies potential/real exception conditions as a function of mapping the current biometric data feeds against the original biometric signature 29.

In normal operation, there is a high degree of mapping and adherence of current biometric data to that of the original biometric signature 29 derived during calibration. Any significant deviation from any/all parameters is identified as a potential exception value. The cause of this could vary from a change in activity application (from rest to exertion) or a change in environment (temperature, respiration). A real exception value is a result of a change in host (skin definition 24, ECG 26) or an unscheduled missing signal.

Such deviations in biometric signature 29 form part of the acceptable behaviour parameters which are constructed and profiled for any host.

The mobile unit 4 follows the following top-level sequence of operations during active mode:
  While power is available
  take local biometric readings every 30 seconds
  verify local storage 14 is available
  delete data over 5 minutes old
  store biometric data as current signature 29
  verify signature data 29 against original calibrated signature 29
  compute GPS co-ordinates every 5 minutes
  verify GPS data in accordance with behaviour rules TSR Agent 16
  If any exception conditions exist then
    Create PDU with biometric, operational and GPS data
    Send PDU to a control centre 33 (see FIG. 2) via relevant communications module 9

Figure 2:
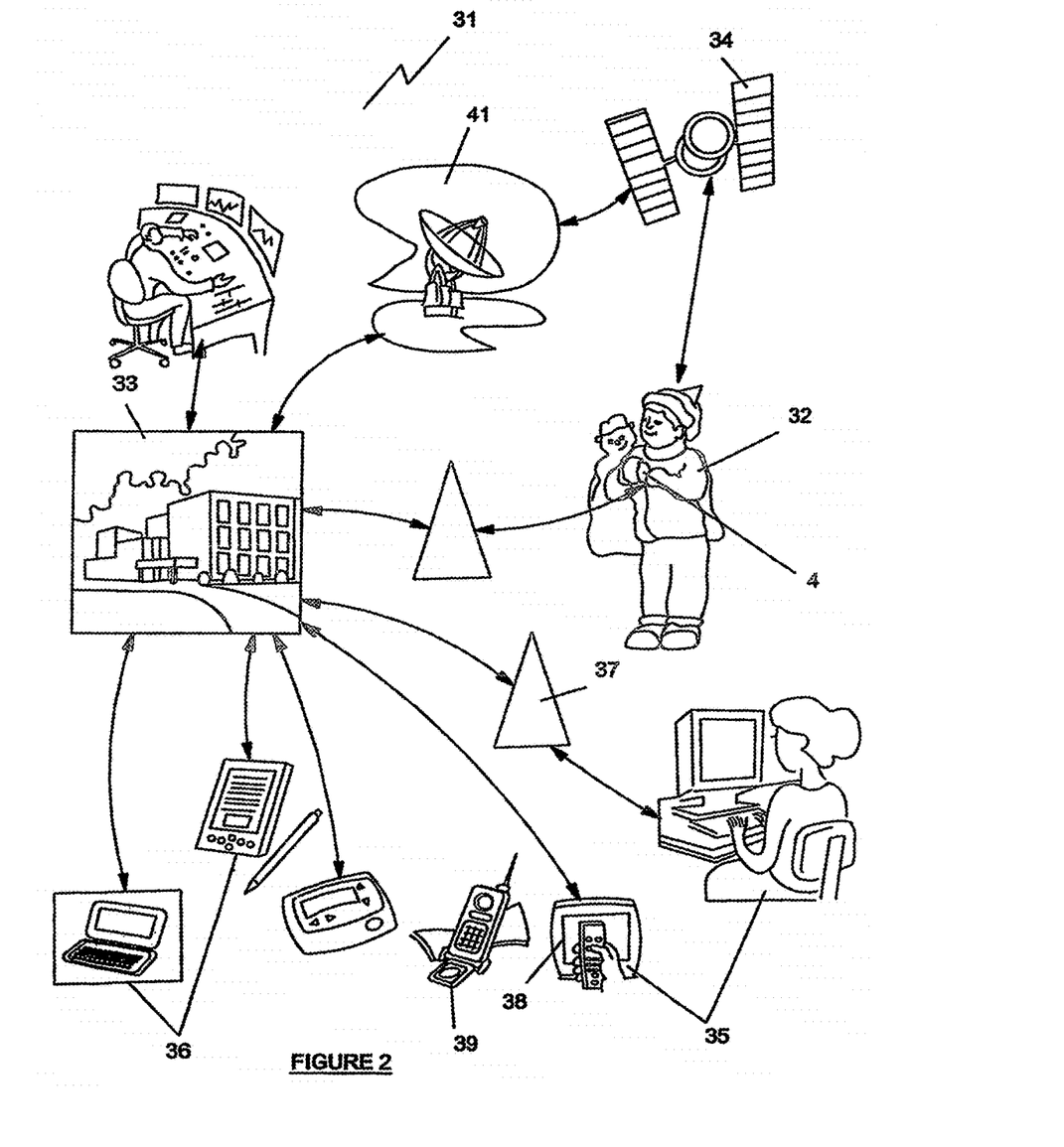
FIG. 2 is a pictorial drawing of a system for monitoring and tracking a host wearing the mobile unit.

The mobile unit 4 follows the following sequence of operation during passive mode:—
  While power is available
  If a request for a PDU from a control centre is received or a Local Alarm signal activated then
    take local biometric readings
    verify local storage 14 is available
    store biometric data as current signature 29
    compute GPS co-ordinates
    Create PDU with biometric, operational and GPS data
    Send PDU to the control centre 33 via a relevant communications module 9

On receipt of the relevant PDU from the unit 4 the control centre 33 determines if any attribute of the PDU represents an exception condition based on:
  host alarm signal activated manually
  host alarm signal activated automatically (tamper)
  host raised exception condition (spatial rule violation)
  host raised exception condition (biometric calibration violation)

The unit 4 either discovers that the exception condition has occurred on GPS or biometric attributes and informs the control centre 33, or the passive mode will return a PDU and the control centre 33 processes the data against its behaviour rule database for this host. If the data passes the TSR agent 16 then the operational mode is maintained as normal.

The host has the ability to switch off the unit 4 and remove the biosensor 23 at pre-determined locations and events (including when at home, sleeping, travelling by train/ aeroplane, swimming). In all these situations, the transition to either power-off or the switching off of key components of the device in order to reduce power consumption is pre-programmed into the behaviour rules TSR agent 16.

The power consumption level is monitored and reported under operational data as part of the PDU which is sent back to the control centre 33. The unit 4 raises an exception condition on the level of battery life available if the status become critical (i.e. less than 25% power level is reached). In such an event, the control centre 33 processes the PDU and forwards the status to the relevant contact point for this host. In order to conserve power under normal operational conditions, the unit 4 will use trickle power mode of operation when applicable.

Referring now to FIG. 2, there is shown a pictorial representation of a system of the invention indicated generally by the reference numeral 31. The system 31 has a mobile unit 4 secured on the wrist of a child 32. The mobile unit 4 is in freespace communication with a control centre 33 and a GPS satellite 34. The control centre 33 and a parent/ guardian or interested third party 35 are in communication via the internet through an ISP 37. Other apparatus and modes of communication between the control centre 33 and a third party 35 include interactive TV 38 via ADSL, mobile phones 39 via GSM and PDA's 36 via GPRS. An earth transceiver station 41 is shown in freespace communication with both the GPS satellite 34 and the control centre 33.

In the normal mode of operation, a GPS unit 28 (see FIG. 1) in the mobile unit 4 is turned off and the system for communication with the control centre 33 is placed in listening mode similar to a GPRS-enabled mobile device.

When the control centre 33 communicates with the mobile unit 4, either as a systems check or because the parent/guardian 35 wishes to determine the state of the child 32, the control centre 33 initiates a communications channel with the unit 4 using a wireless circuit via GSM/GPRS/ 802.11, cellular, MIP, which relays the signal to the mobile unit 4. In receipt of such a signal from the control centre 33, the mobile unit 4 executes a TSR 16 which allows it to return a signal indicating the unit 4 is active containing:—
  spatial location data
  operational status/battery power level\
  biometric signature data The GPS transceiver 28 on the mobile unit 4 can calculate its spatial co-ordinates via a GPS satellite 34 as a function of time and space and pass this back as spatial location data.

Should the child 32 be out of range of normal wireless protocols, the system 31 can use GPS to provide the transmit/receive flow from/to the control centre 33 from the mobile unit 4. In situations where the host 32 is at sea, in mountainous terrain, in desert surroundings, it is necessary to provide satellite communications only so that the mobile unit 4 can be uniquely identified, addressed and accessed. The same TSR 16 is executed by the mobile unit 4 on receipt of the request from the control centre 33. Without such intervention the mobile unit 4 is out of range. The mobile unit 4 sends periodic data feeds in accordance with the attributes of the unit 4 itself.

Depending on the activity and the physical location of the host 32, the control centre 33 communicates with the host 32 via GPS modules 28 or other communications interfaces 9 using IEEE 802.11, 3G, GPRS, GSM, Bluetooth. The mobile unit 4 responds to the control centre 33 accordingly under the control of the processor 10 of the microcontroller.

In general, when the unit 4 detects an exception condition locally it uses mobile communications to initiate a communications session with the control centre 33. The GPS unit 28 performs the location function utilising signals from the GPS satellite 34 nearby. Under normal operations, the GPS module 28 is powered off unless either the unit 4 has detected a biometric e2weption condition, the host has issued an alarm 12 or the control centre 33 requests a status update. In such events, the GPS modules 28 are turned on and the location process is executed under the control of the processor 10. The GPS components 34, 28 may combine other data from the control centre 33 to verify and refine the results. Such aiding data may include approximate location data, an almanac ephemeris, a frequency offset, doppler, previous spatial reference, time, etc. The GPS components 34, 28 provide the spatial location data computed using the GPS satellite 34 in connection with the GPS unit 28 and the processor 10. This data is then combined with the biometric signature 29 and sent as a structured PDU to the control centre 33 via appropriate communications protocols.

Operational data concerning power source levels of the power sources 19, 22 (see FIG. 1) is also included. Upon receipt of the PDU the control centre 33 verifies the values of the PDU attributes in accordance with the behaviour rules database 17 for that target host at that specific point in time and space.

If the PDU came from the unit 4 as a result of a user-initiated Alarm 12, then the control centre 33 expedites the alarm condition to the named contact person/organisation on the database who is to be contacted in an emergency. If, however, the PDU came from the mobile unit 4 in either a response to an earlier request from a control centre 33, or as a potential exception condition detected by the unit 4 itself, the control centre 33 verifies the PDU attributes in accordance with the behaviour rules database 17 for that target host 1 at that specific point in time and space and responds accordingly.

Figure 3:
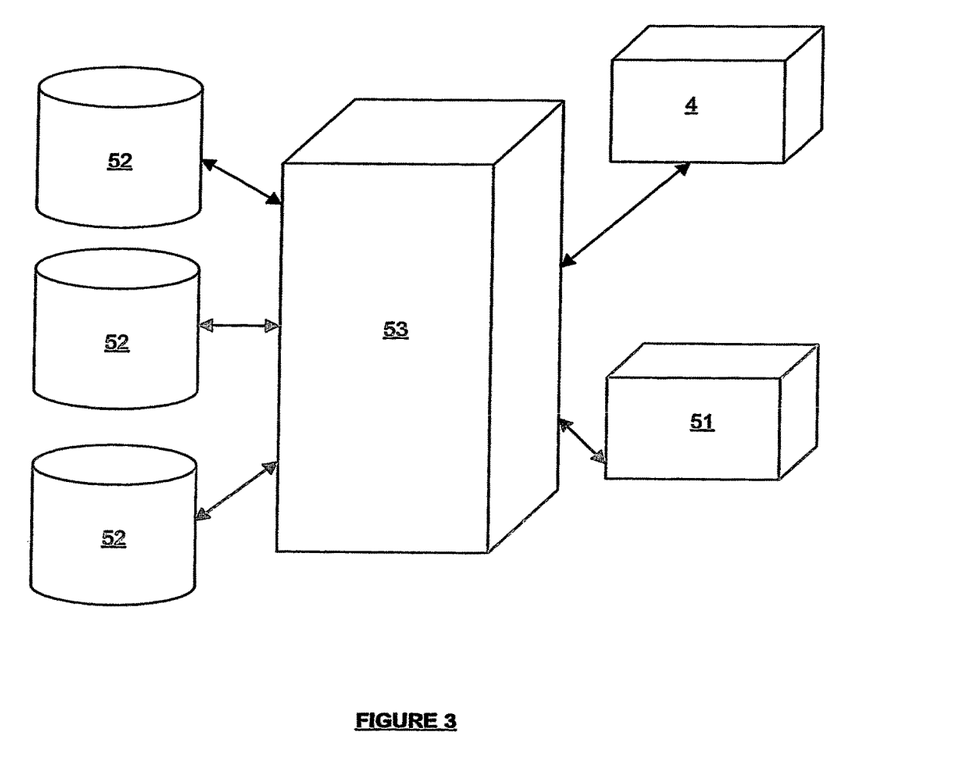
FIG. 3 is a schematic representation of the process of scripting the behaviour rules.

Referring now to FIG. 3, the behaviour rules are defined via a scripting language and programmed via a web-based graphical upper interface (GUI) by the control centre 33 or the parent/guardian 35 of the host 32. The spatial and biometric rules that define the acceptable movement and status of the host 32 as a function of time, space and activity are programmed as follows. The method by which the behavioural rules are structured, defined and expressed is by means of a script 52 which is written in either C or Java and verified through a script compiler 53. Essentially, the script 52 is a means by which the assumed location and activity of the host are defined as a function of time of day and activity. The script 52 is combined with the status of the host 32 in term§ of their key biometric readings. Such biometric parameters will relate to body temperature, dermis, ECG attributes.

Each script 52 will also contain the parameter values for:—
Date (date)
time (24 hour clock) (numeric)
x, y co-ordinates from the national grid (numeric)
location descriptor (text)
i. home
ii. School
iii. Holiday
iv. Shopping
v. Work
vi. etc.
activity descriptor (text)
i. field sport
ii. Swimming
iii Climbing
iv. Skiing
v. indoor sport
vi. leisure
vii. school
viii. work
ix. etc.
appointed trustee (if any)
mode of transport
i. (on foot, car, bicycle, surface train, plane, ship, underground, etc.)
biometric attributes
i. body temperature
ii. ECG parameters
iii. Skin type
iv. Perspiration level
v. Tee.

For each physical communication protocol which is emulated within the host 32, there will be associated with it a range of scripts 52 which will be sent to the unit 4 via a script dispatcher 51 and executed by the unit 4 and subsequently used to enter into a dialogue with the control centre 33.

These are then assembled into executable mobile agent code for transmission to the unit 4 as a TSR 16. Mobile client-server protocols are enabled to provide for the call-set-up, agent communications and TSR 16 verification between the control centre 33 and the unit processor 10. The behavioural rules database 17 is then populated with these values. Subsequent local datafeeds from GPS 28 and Biometric sensor 23 are compared against the behavioural database 17 and the rules that were defined in the TSR 16. A Data warehouse will be maintained at the control centre 33 to keep a profile of the host behaviour for future reference and prediction.

Variations and modifications can be made without departing from the scope of the 10 invention described above and as hereinafter defined in the appended claims.

The invention claimed is:

1. A programmable mobile unit that is wearable by a host person, comprising:
    a detachable freespace communication module for communication with a control center;
    a GPS unit operable to take up communication with at least a GPS satellite system;
    a biometric sensor arranged to monitor the host person and thereby obtain biological data specific to the host person, the biometric sensor comprising a plurality of body contacting elements; and
    a microcontroller operable to take up communication with each of the communication module, the GPS unit and the biometric sensor, and to process the biological data in order to identify the host person by mapping the biological data against a biometric signature;
    wherein the programmable mobile unit is wearable on a wrist of the host person;
    wherein the microcontroller includes an interpretation program stored in a memory of the microcontroller;
    wherein the interpretation program detects exception values falling outside allowable tolerances defined in a database stored in the memory of the microcontroller;
    wherein the interpretation program prioritizes the exception values falling outside allowable tolerances defined in the database;
    wherein the interpretation program selects those exception values which indicate that the host person is encountering significant difficulties;
    wherein the microcontroller transmits the selected exception values to the control center via the communications module in communication with the microprocessor.

2. The programmable mobile unit as claimed in claim 1, wherein the detachable freespace communication module selectively switches between different freespace communication protocols for communicating with the control center.

3. The programmable mobile unit as claimed in claim 1, wherein the memory of the microcontroller includes a database of acceptable behavior parameters for the host person.

4. The programmable mobile unit as claimed in claim 3, wherein the database defines the boundaries of acceptable geographical locations and acceptable biological values as a function of time for the host person.

5. The programmable mobile unit as claimed in claim 3, wherein the database is remotely programmable to take new activities and routines of the host person into account.

6. The programmable mobile unit as claimed in claim 1, wherein an initial identification of the host person takes place during a learning phase when the biometric sensor is first attached to the host person and the mobile unit is initially powered up.

7. The programmable mobile unit as claimed in claim 6, wherein the initial identification provides a reproducible, identifiable biometric signature for the host person.

8. The programmable mobile unit as claimed in claim 1, wherein the biometric sensor comprises a power source and a flexible multi-sensor patch which continuously monitors the host person's ECG, body temperature and respiration rate.

9. The programmable mobile unit as claimed in claim 1, wherein the biometric sensor is provided with flexible circuitry allowing the sensor to adapt to the shape of the host person's body.

10. The programmable mobile unit as claimed in claim 1, wherein the biometric sensor and the microcontroller communicate using Bluetooth technology.

11. The programmable mobile unit as claimed in claim 1, wherein the microcontroller is pre-programmed to periodically monitor and download up-to-date information from the GPS unit and the biometric sensor.

12. A system for monitoring and tracking a person wearing a programmable mobile unit, comprising:
   a programmable mobile unit which is wearable on a wrist of a host person, comprising:
   a. a detachable freespace communication module for communication with a control center;
   b. a GPS unit operable to take up communication with at least a GPS satellite system;
   c. a biometric sensor arranged to monitor the host person and operable to obtain biological data specific to the host person, wherein the biometric sensor comprises a plurality of body contacting elements; and
   d. a microcontroller operable to take up communication with each of the communication module, the GPS unit and the biometric sensor, and to process the biological data in order to identify the host person by mapping the biological data against a biometric signature; and
   a control center in freespace communication with said mobile unit and a GPS satellite system;
   wherein the microcontroller includes an interpretation program stored in a memory of the microcontroller;
   wherein the interpretation program detects exception values falling outside allowable tolerances defined in a database stored in the memory of the microcontroller;
   wherein the interpretation program prioritizes the exception values falling outside allowable tolerances defined in the database;
   wherein the interpretation program selects those exception values which indicate that the host person is encountering significant difficulties;
   wherein the microcontroller transmits the selected exception values to the control center via the communications module in communication with the microprocessor.

13. The system as claimed in claim 12, wherein the mobile unit and the control center periodically communicate with each other using freespace communication protocols.

14. The system as claimed in claim 12, wherein an acceptable behavior database of acceptable behavior parameters for the host person is stored at the control center and on the mobile unit.

15. The system as claimed in claim 14, wherein the system includes a web-based interface to a database driven secure environment for dynamic creation and modification of the acceptable behavior database stored in the control center and the mobile unit.

16. The system as claimed in claim 12, wherein the control center of the system and third parties are in communication using predetermined communication protocols.

17. The system as claimed in claim 12, wherein the control center includes means for alerting custodians and third parties of the selected exception values via predetermined communication protocols.

18. The system as claimed in claim 16, wherein the third parties and the control center have means for contacting the mobile unit via predetermined communication protocols.

19. The programmable mobile unit as claimed in claim 1, wherein, during a learning phase, the microcontroller is configured to identify the host person by:
   generating and transmitting signals into the body of the host person;
   receiving signals from the host person's body after they have been attenuated by the bioelectrical impedance of the host person's body; and
   analyzing the attenuated signals to produce a bioelectrical impedance signature capable of identifying the host person, wherein the bioelectrical impedance signature forms at least a part of the identifiable biometric signature.

20. The programmable mobile unit as claimed in claim 19, wherein, in a normal operation mode entered after the learning phase, the microcontroller is configured to check for exception values falling outside acceptable tolerances by:
   comparing the bioelectrical impedance signature of the host person recorded during said learning phase with a live bioelectrical impedance signature recorded from the host person's body.

21. The programmable mobile unit as claimed in claim 1, wherein, to identify the host person, the microcontroller is configured to:
   compare a bioelectrical impedance signature of a host person recorded during a secure enrolment with a live bioelectrical impedance signature recorded from the host person's body.

22. The programmable mobile unit as claimed in claim 1, wherein the microcontroller is configured to generate a real exception value signifying a change in host person wearing the mobile unit responsive to a change in at least one of:
   skin definition and ECG.

23. A control program embedded on a non-transitory computer readable medium, executable on a microcontroller of a programmable mobile unit as claimed in claim 1, to cause the programmable mobile unit to:

receive, by the microcontroller, information from the GPS unit and the biometric sensor and to store said information;

access, by the microcontroller, a database of acceptable behavior parameters for a host person, said database defining the boundaries of acceptable behavior for the host person including acceptable geographical locations for the host person in addition to acceptable biological values; and compare, by the microcontroller, the information received from the GPS unit and the biometric sensor against the database;

wherein the microcontroller includes an interpretation program stored in a memory of the microcontroller;

wherein the interpretation program detects the exception values falling outside allowable tolerances defined in the database;

wherein the interpretation program prioritizes the exception values falling outside allowable tolerances defined in the database;

wherein the interpretation program selects those exemption values which indicate that the host person is encountering significant difficulties;

wherein the microcontroller transmits the selected exemption values to a control center via a communications module in communication with the microprocessor.

24. The control program as claimed in claim 23, wherein the control program is executable on the microcontroller to cause the microcontroller to be operable to periodically monitor and download up-to-date information from the GPS unit and the biometric sensor.

25. The control program as claimed in claim 23, wherein the acceptable biological values include at least one of:
body temperature, heart rate and bioelectrical impedance at any given point in time.

26. The control program as claimed in claim 23, wherein the control program is executable on the microcontroller to cause the microcontroller to compare the information received from the GPS unit and the biometric sensor against the database every time new location and biometric information is captured and downloaded from both the biometric sensor and the GPS unit.

27. The programmable mobile unit as claimed in claim 1, wherein the biometric sensor comprises an ECG.

28. The system as claimed in claim 12, wherein the biometric sensor comprises an ECG.

* * * * *